United States Patent
Barbieri et al.

(10) Patent No.: US 11,390,645 B2
(45) Date of Patent: Jul. 19, 2022

(54) PROCESS FOR THE PREPARATION OF 3β-HYDROXY-17-(1H-BENZIMIDAZOL-1-YL) ANDROSTA-5,16-DIENE

(71) Applicant: INDUSTRIALE CHIMICA S.R.L., Milan (IT)

(72) Inventors: Francesco Barbieri, Azzate (IT); Roberto Lenna, S. Giorgio su Legnano (IT)

(73) Assignee: INDUSTRIALE CHIMICA S.R.L., Milan (IT)

( * ) Notice: Subject to any disclaimer, the term of this patent is extended or adjusted under 35 U.S.C. 154(b) by 569 days.

(21) Appl. No.: 16/323,317

(22) PCT Filed: Aug. 8, 2017

(86) PCT No.: PCT/EP2017/070124
§ 371 (c)(1),
(2) Date: Feb. 5, 2019

(87) PCT Pub. No.: WO2018/029223
PCT Pub. Date: Feb. 15, 2018

(65) Prior Publication Data
US 2021/0284681 A1    Sep. 16, 2021

(30) Foreign Application Priority Data

Aug. 8, 2016  (IT) .......... 102016000083406
Nov. 30, 2016  (IT) .......... 102016000121375

(51) Int. Cl.
C07J 43/00    (2006.01)
C07J 75/00    (2006.01)

(52) U.S. Cl.
CPC ............ *C07J 43/003* (2013.01); *C07J 75/00* (2013.01)

(58) Field of Classification Search
CPC .................................................. C07J 43/003
See application file for complete search history.

(56) References Cited

FOREIGN PATENT DOCUMENTS

| WO | WO 2006/093993 A1 | 9/2006 | | |
|---|---|---|---|---|
| WO | WO 2016/119742 A1 | 8/2016 | | |
| WO | WO-2017140183 A1 | * | 8/2017 | ............ A61K 31/58 |

OTHER PUBLICATIONS

Berge et al. (Journal of Pharmaceutical Sciences, 1977, 66(1), pp. 1-19) .*
International Search Report dated Nov. 17, 2017 issued in PCT/EP2017/070124.
Handratta Venkatesh D et al: "Novel C-17-Heteroaryl Steroidal CYP17 Inhibitors/Antiandrogens: Synthesis, in Vitro Biological Activity, Pharmacokinetics, and Antitumor Activity in the LAPC4 Human Prostate Cancer Xenograft Model", Journal of Medicinal Chemistry, American Chemical Society, US (Mar. 25, 2005), vol. 48, No. 8, pp. 2972-2984.
Vincent C. O. NJAR et al: "Discovery and Development of Galeterone (TOK-001 or VN/124-1) for the Treatment of All Stages of Prostate Cancer", Journal of Medicinal Chemistry (Mar. 12, 2015), vol. 58, No. 5, pp. 2077-2087.
Gerard A. Potter et al: "A Convenient, Large-Scale Synthesis of Abiraterone Acetate [3[beta]-Acetoxy-17-(3-Pyridyl) Androsta-5, 16-Diene], a Potential New Drug for the Treatment of Prostate Cancer", Organic Preparations and Procedures International (Feb. 1, 1997), vol. 29, No. 1, pp. 123-128.
Clement, Omoshile O. et al., "Three Dimensional Pharmacophore Modeling of Human CYP17 Inhibitors. Potential Agents for Prostate Cancer Therapy", J. Med. Chem. (2003), vol. 46, No. 12, pp. 2345-2351.

* cited by examiner

*Primary Examiner* — Susanna Moore
(74) *Attorney, Agent, or Firm* — Scully, Scott, Murphy & Presser, P.C.

(57) ABSTRACT

A process for the synthesis of β-hydroxy 3-17-(1H-benzimidazol-1-yl)androsta-5,16-diene is described, a compound also known as Galeterone and used in the treatment of prostate cancer, having the formula (6).

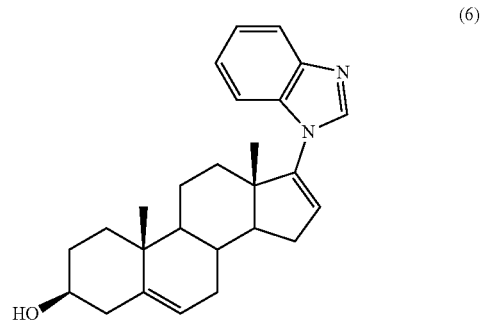

(6)

15 Claims, 3 Drawing Sheets

PROCESS FOR THE PREPARATION OF 3β-HYDROXY-17-(1H-BENZIMIDAZOL-1-YL) ANDROSTA-5,16-DIENE

FIELD OF THE INVENTION

The present invention relates to the field of processes for the synthesis of active ingredients for pharmaceutical use, and in particular to a process for the industrial-scale preparation of 3β-hydroxy-17-(1H-benzimidazol-1-yl)androsta-5,16-diene, also known as Galeterone, a compound useful for the treatment of prostate cancer, having the following formula:

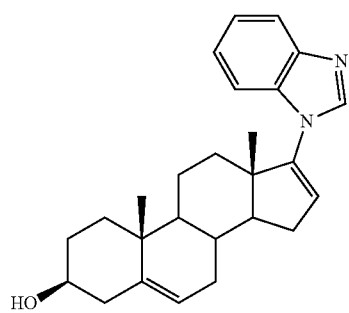 [SMILES: C[C@]12CC[C@H](O)CC1=CCC1C2CC[C@]2(C)C(n3cnc4ccccc43)=CCC12]

PRIOR ART

Galeterone, 3β-hydroxy-17-(1H-benzimidazol-1-yl)androsta-5,16-diene was first described in the article "Three dimensional pharmacophore modeling of human CYP17 inhibitors. Potential agents for prostate cancer therapy", O. Omoshile et al., J. Med. Chem. 2003, 46 (12), pages 2345-2351, in Figure 1 on page 2347, with the abbreviation VN/124-1*. The article does not report an experimental description of the preparation of the molecules object of the text, among which Galeterone, but refers to several other publications for the synthesis thereof.

Among the publications cited in the article by Omoshile et al., a significant one is "Novel 17-azolyl steroids, potent inhibitors of human cytochrome 17α-Hydroxylase-$C_{17,20}$-lyase ($P450_{17α}$): potential agents for the treatment of prostate cancer", V. C. O. Njar et al., J. Med. Chem., 1998, 41 (6), pages 902-912, which describes the sequence of reactions that, explicitly recalled and described in J. Med. Chem. 2005, 48, 2972-2984, leads to obtaining Galeterone.

The first synthetic step is described in "Novel C-17-Heteroaryl steroidal CYP17 inhibitors/antiandrogens: synthesis, in vitro biological activity, pharmacokinetics, and antitumor activity in the LAPC4 human prostate cancer xenograft model", V. D. Handratta et al., J. Med. Chem., 2005, 48 (8), pages 2972-2984. This synthetic step consists of a Vilsmeier-Haack reaction which uses as a starting material 3β-acetoxyandrosta-5-en-17-one (1) to yield 3β-acetoxy-17-chloroandrosta-5,16-diene (2) and 3β-acetoxy-17-chloro-16-formylandrosta-5,16-diene (3), as shown in the following scheme:

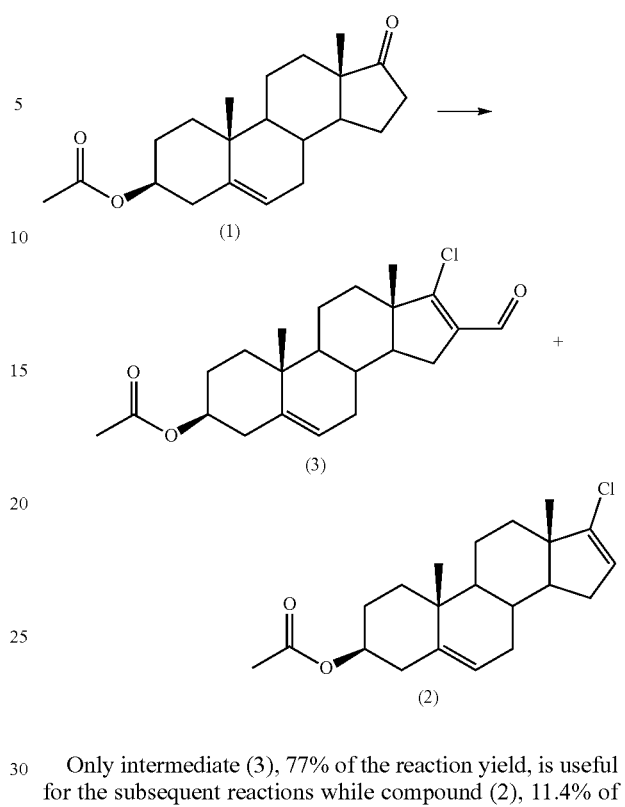

Only intermediate (3), 77% of the reaction yield, is useful for the subsequent reactions while compound (2), 11.4% of the reaction yield, must be discarded.

In the above article by Njar et al., the separation of the two reaction products is obtained by flash chromatography (FCC) on silica gel.

The synthesis described in the article by Handratta et al. starts from compound (3) prepared as described above; compound (3) is reacted with benzimidazole, thus yielding the intermediate 3β-acetoxy-17-(1H-benzimidazol-1-yl)-16-formylandrosta-5,16-diene (4):

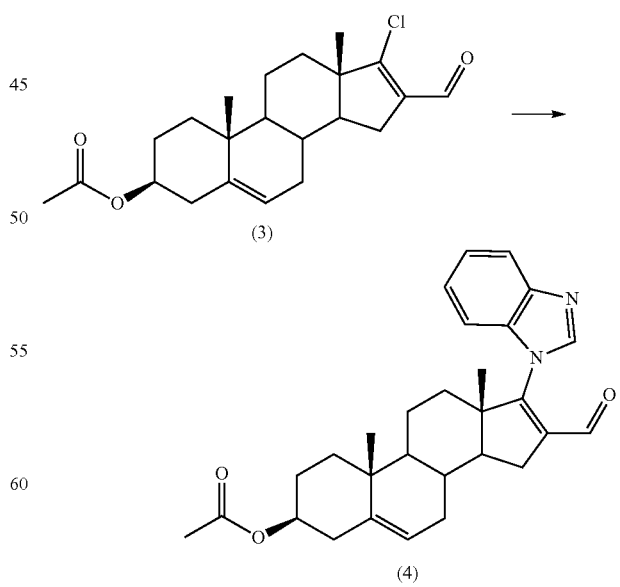

The purification of intermediate (4) is obtained by flash chromatography (FCC) on silica gel.

Intermediate (4) is then thermally deformylated using 10% palladium on carbon (Pd/C) as catalyst in an amount equal to 50% of the weight of intermediate (4):

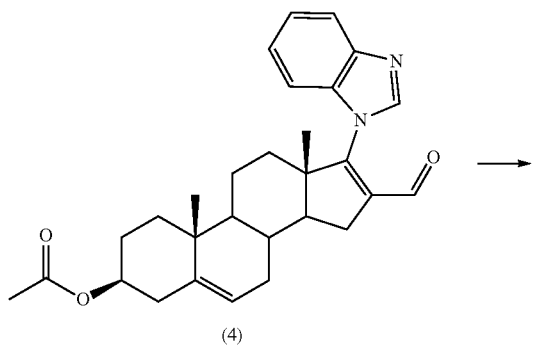

(4)

The purification of intermediate (5) is obtained by flash chromatography (FCC) on silica gel.

Finally, intermediate (5) is deacetylated in bases and the crude Galeterone (6) is crystallized from the ethyl acetate/methanol mixture:

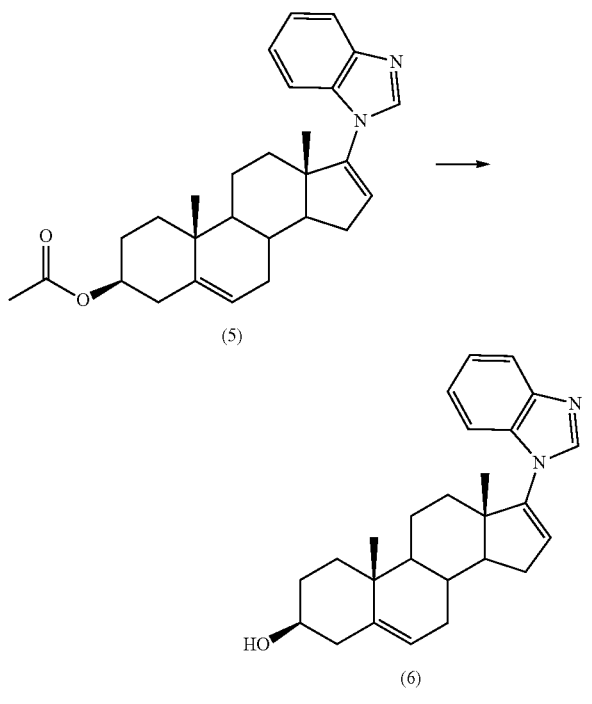

As with the reactions above, no quality data (titer and HPLC purity) are provided in the experimental descriptions.

SUMMARY OF THE INVENTION

The object of the present invention is to provide a synthesis route for the preparation of Galeterone that is simpler than the prior art processes and easily industrially applicable.

This object is achieved by means of the present invention that, in a first aspect thereof, relates to a process for the preparation of Galeterone (6) comprising the reaction between 17-iodoandrosta-5,16-dien-3β-ol (I) and benzimidazole to yield 3β-hydroxy-17-(1H-benzimidazol-1-yl)androsta-5,16-diene (6) (Galeterone):

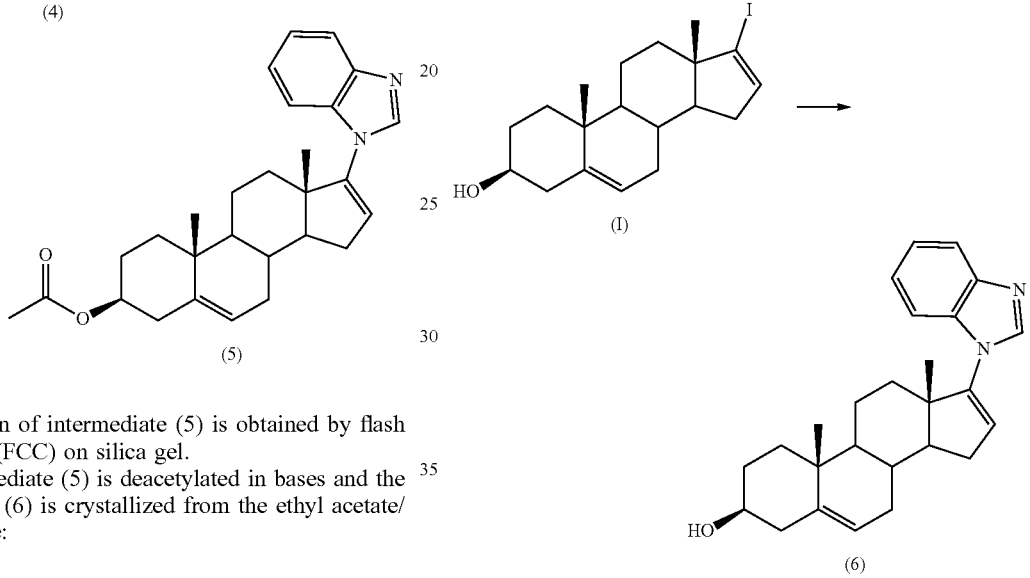

In a second aspect thereof, the invention relates to separation by filtration from the reaction mixture of the compound obtainable by reaction of Galeterone with a physiologically acceptable organic or inorganic acid, this compound being useful for the purification of the desired product.

Preferably, the Galeterone di-oxalate is separated by filtration.

In a third aspect, the invention relates to salts obtained by reaction with Galeterone, which are employed for the purification thereof.

DETAILED DESCRIPTION OF THE INVENTION

Figure 1:
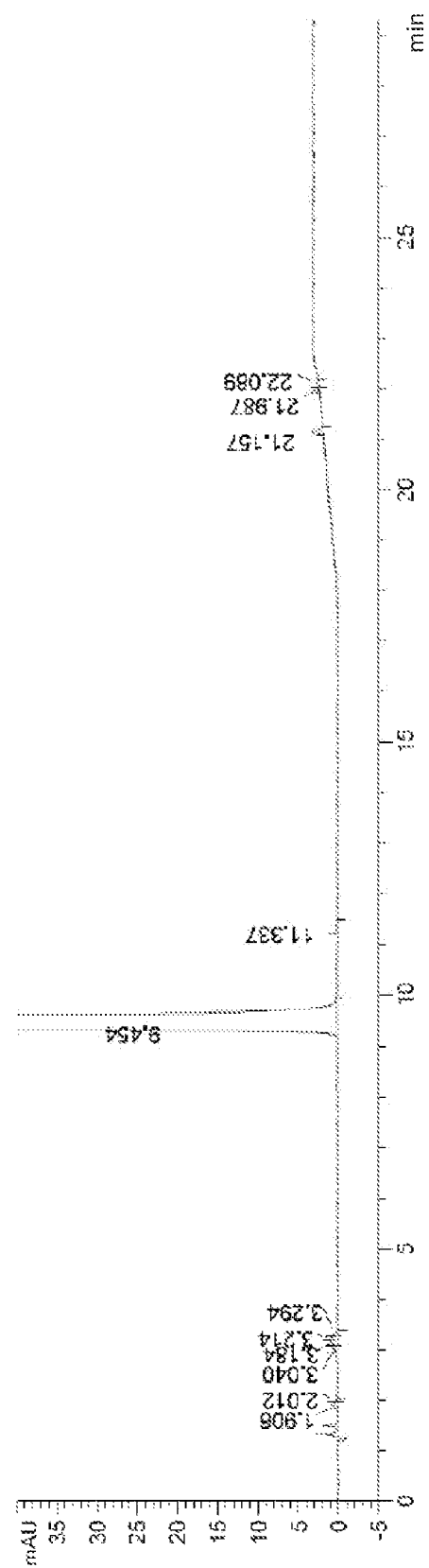
FIGS. 1, 2 and 3 show the results of HPLC analysis of products obtained according to the process of the invention.

In a first aspect thereof, the invention relates to a synthesis process of Galeterone (6) that is industrially applicable, comprising the steps described in detail hereinafter.

In the present description and in the claims, in the event of a discrepancy between the chemical name of a compound and the formula given for the same, the latter must be regarded as correct.

The step object of the invention consists in the reaction between 17-iodoandrosta-5,16-dien-3β-ol (I) and benzimidazole in the presence of a base, of 8-hydroxyquinoline and cuprous iodide as catalysts to yield 3β-hydroxy-17-(1H-benzimidazol-1-yl)androsta-5,16-diene (6) also known as Galeterone:

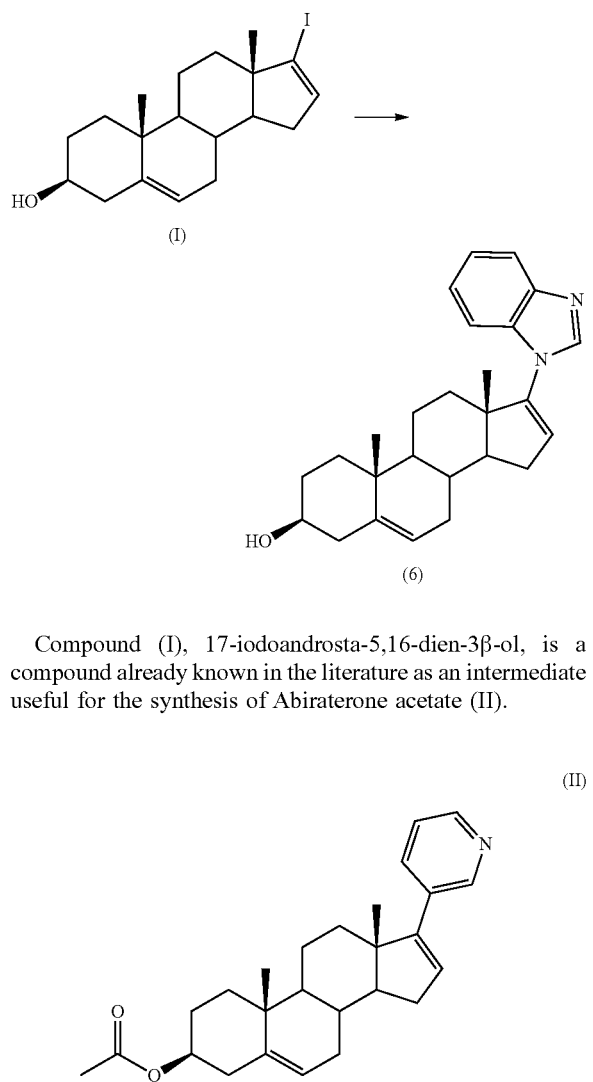

Compound (I), 17-iodoandrosta-5,16-dien-3β-ol, is a compound already known in the literature as an intermediate useful for the synthesis of Abiraterone acetate (II).

The preparation of compound (I) 17-iodoandrosta-5,16-dien-3β-ol is described in Organic Preparations and Procedures Int., 29(1), 123-134 (1997) within the description of the synthesis of Abiraterone acetate.

The reaction object of the present invention is carried out in a single organic solvent in the presence of benzimidazole, a base, cuprous iodide (CuI) and 8-hydroxyquinoline (organic ligand). In cuprous iodide, copper is present in oxidation state +1, and the compound is normally indicated in the literature with the notation copper (I) iodide, wherein (I) indicates said oxidation state; in the present text and in the claims, only the name "cuprous iodide" or the formula CuI will be adopted to avoid confusion with compound (I), reagent in the reaction of the invention.

The organic solvent is selected among dimethylformamide (DMF), dimethylacetamide (DMA), dimethylsulfoxide (DMSO) and 1,3-dimethyl-3,4,5,6-tetrahydro-2 (1H)-pirimidinone (DMPU), and is employed in an amount between 5 and 20 times by volume, measured in ml, with respect to the weight in g of compound (I) loaded in the reaction (concentration (v/w)).

The preferred solvent is dimethylformamide, and it is preferably used in a volume of between 5 and 10 times the weight (v/w) of compound (I).

The reaction temperature is of between 130° C. and 200° C.

A reaction test carried out with microwave reactor maintaining the reaction mixture at 200° C. for 1 h showed no degradation of the starting compound (I) or of the resulting Galeterone (6).

Preferably, the reaction temperature is between 140° C. and the boiling temperature of the reaction mixture as obtained after the addition of all components.

The reaction time is between 12 and 48 hours, preferably between 14 and 24 hours.

As organic ligand, 8-hydroxyquinoline, 2-hydroxyquinoline, 3-hydroxyquinoline, 4-hydroxyquinoline and 6-hydroxyquinoline were tested. The formation of Galeterone is observed only by employing 8-hydroxyquinoline.

8-hydroxyquinoline is used in an amount by weight of at least 1.8% with respect to the weight of compound (I) employed in the reaction. Preferably, an amount of 8-hydroxyquinoline equal to 3.6% of the weight of compound (I) loaded in the reaction is used.

The base employed may be selected from sodium carbonate, potassium carbonate, cesium carbonate, sodium tert-butylate, potassium tert-butylate, sodium hydroxide and potassium hydroxide.

Preferably, potassium carbonate ($K_2CO_3$) is used.

The base is used in an amount by weight of at least 40%, and preferably at least 80%, with respect to the weight of compound (I).

Benzimidazole is used in an amount by weight of at least 30%, preferably at least 36%, with respect to the weight of compound (I).

The CuI catalyst is used in an amount by weight of between 1.2% and 5% of the weight of compound (I). Preferably, an amount by weight of CuI equal to 2.4% with respect to the weight of compound (I) is used.

The crude Galeterone obtainable from the reaction, carried out following the indications referred to above, can be purified by subjecting it to chromatography on silica gel and crystallizing it from organic solvent according to the common techniques known in the field of organic synthesis.

However, the inventors have surprisingly verified that the preparation of a Galeterone compound with an acid and its separation from the reaction mixture by simple filtration proves to be a particularly effective method for reaching, without resorting to chromatographic purifications, the levels of purity that an active ingredient requires to be used in pharmaceutical compositions. As acids, physiologically acceptable inorganic or organic acids may be used, such as hydrochloric acid, hydrobromic acid, sulfuric acid, phosphoric acid, acetic acid, propionic acid, maleic acid, citric acid, lactic acid, oxalic acid, benzoic acid, fumaric acid, succinic acid, tartaric acid and xinafoic acid; these acids can be used in anhydrous or hydrated form.

Preferably, oxalic acid hydrate is used as acid, in amounts of at least two moles of acid per mole of Galeterone to be purified, obtaining Galeterone dioxalate, of formula:

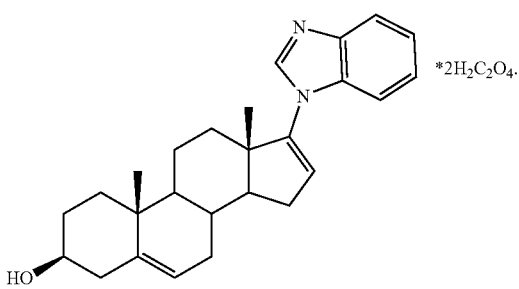 [SMILES: C[C@]12CC[C@H](O)CC1=CCC1C2CC[C@]2(C)C(n3cnc4ccccc43)=CCC12]

After eliminating most of the catalyst by filtration, the solution in which Galeterone has formed can be treated with a metal scavenging agent to eliminate any residual amounts of metal possibly present; suitable for the purpose are the products of the QuadraSil® family sold by Sigma-Aldrich, in particular the QuadraSil® MP product, consisting of spherical particles of macroporous silica functionalized to remove residual metals from products containing them (QuadraSil® is a registered trademark of the company Johnson Matthey).

The formation of Galeterone dioxalate takes place by reaction of Galeterone with oxalic acid in an organic solvent solution, from which the dioxalate separates as filterable solid.

After filtration, the dioxalate is washed with a suitable solvent, e.g. toluene, methylene chloride or acetonitrile, dried (conveniently under reduced pressure), then re-suspended in a suitable organic solvent and treated with a base, added either pure or dissolved in a solvent, to recover pure Galeterone.

The organic solvent in which the dioxalate is suspended is selected from xylene, toluene, cyclohexane, heptane, hexane, methylene chloride and acetonitrile, either pure or mixed with each other; the preferred solvent for this operation is pure methylene chloride.

The base is selected from sodium hydrogen carbonate, potassium hydrogen carbonate, sodium hydroxide, lithium hydroxide, potassium hydroxide, sodium carbonate, cesium carbonate and potassium carbonate, dissolved in water or in an alcohol such as methanol, ethanol, isopropanol; preferably it is used sodium hydroxide dissolved in methanol.

The invention will be further illustrated by the following examples.

Instruments, Methods and Test Conditions

NMR

Spectrometer NMR JEOL 400 YH (400 MHz); Tubes NMR Aldrich® ColorSpec®;

JEOL Delta Software v5.1.1;

Spectra recorded in deuterated chloroform Sigma-Aldrich: Chloroform-d, D 99.8% atomic, containing 0.1% (v/v) tetramethylsilane (TMS) as internal standard; and Chloroform-d, "100%", D 99.96% atomic, containing 0.03% (v/v) TMS.

MS

HPLC-mass system AB Sciex API 2000 LC/MS/MS;

Samples injected directly and chemically ionized (CI).

DSC

Instrument Perkin Elmer mod. Diamond;

Capsules Perkin Elmer Standard aluminum and lids, code 02190041;

Scanning rate: 10° C./min;

Temperature range: 20° C. to 200° C.

IR

Thermo Scientific Nicolet 6700 spectrometer;

FT-IR spectra recorded in KBr (solid) and smart-it-diffuse reflectance (ATR);

Potassium bromide Sigma-Aldrich Code 221864 (for IR analysis).

HPLC

Chromatographic system Agilent model 1200 and 1260;

Detector UV MODEL 1260 DAD VL and Laser Detector 1290 Infinity ELSD.

LC/Ms/Ms System

Chromatographic system Agilent model 1100 with UV DAD detector connected to an API 2000 mass by Applied Biosystems.

Easy Max 102 Mettler Toledo System

Workstation to perform synthesis reactions.

Milestone FlexiWAVE Microwave Reactor

Microwave reactor with two 950 Watt magnetrons with a total output of 1900 Watt;

The Milestone FlexiWAVE consists of a single microwave platform that, in combination with specific accessories, allows performing classic glassware and high-pressure synthesis.

TLC Slides

MERCK: TLC silica gel 60 $F_{254}$ Aluminum sheets 20×20 cm, code 1.0554.0001.

HPTLC Slides

MERCK: HPTLC silica gel 60 $F_{254}$ with concentration zone 10×2.5 cm, code 1.13727.0001.

TLC/HPTLC Detector

Acid solution of cerium phosphomolybdate.

Preparation: 25 g of phosphomolybdic acid hydrate (Aldrich P7390), 10 g of cerium (IV) sulfate hydrate (Aldrich 31606) and 600 mL of water are stirred to dissolution with 60 mL of 95-98% sulfuric acid (Aldrich 258105); this is brought to a final volume of 1000 mL with water; the slide is impregnated with the solution, then heated to blue staining.

UV light at 254 and 366 nm.

General Conditions of Execution of TLC (Unless Otherwise Noted)

Eluent: methylene chloride/methanol 9/1 v/v.

Detector: UV—cerium phosphomolybdic detector.

Reaction sample: 1 mL of reaction mixture in 2 mL water, extracted with 2 mL Isopropyl acetate. Deposited 1 μL.

Slide: TLC silica gel 60 $F_{254}$ Aluminum sheets 20×20 cm.

Rf Starting 0.60-Product 0.52

Reference samples: authentic samples identified by NMR and mass analyses.

Deposition: each control is carried out by placing on the slide the reaction sample, the reference sample of the starting product and of the final product and an artificial mixture of reaction sample with the reference samples.

Solvents and Reagents

The solvents and reagents used in the examples below, unless otherwise indicated, are to be understood of the quality commercially available or obtainable by the preparations described in publications available to the public.

Abbreviations

Abbreviations $R_f$ and RRT used in the examples indicate the delay factor in thin layer chromatography (TLC) and the relative retention time of a compound in high pressure liquid chromatography (HPLC), respectively.

Example 1

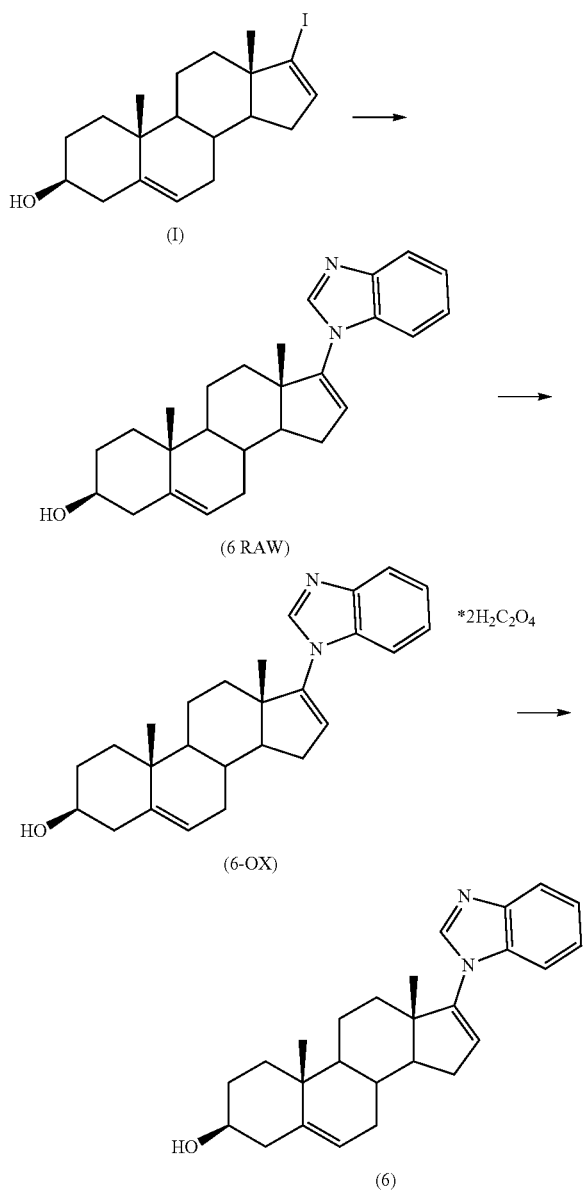

300 g 17-iodoandrosta-5,16-dien-3β-ol (I), 260.45 g K₂CO₃, 106.86 g benzimidazole, 7.18 g CuI, 10.94 g 8-hydroxyquinoline and 1.5 L DMF are loaded to a flask under nitrogen and it is brought to reflux for 16 hours.

At a TLC check carried out at the end of this period, the reaction is complete.

It is cooled to 25° C., the mixture is poured onto 6 L water and stirred for 15 minutes. It is filtered and the resulting solid is washed with water.

The solid is dissolved in 3 L methylene chloride (CH₂Cl₂), obtaining a biphasic system; 1 L water, 6 g carbon, 15 g dicalite are added and it is stirred for 10 minutes. It is filtered washing the filter with 300 mL CH₂Cl₂.

The phases are separated and the organic phase is washed with 300 mL of saturated aqueous solution of NaCl.

15 g QuadraSil® MP are loaded, it is stirred for 16 hours at 20<T<25° C., filtered on Millipore (JGWP) membrane, washing with 50 mL CH₂Cl₂.

The organic phase is concentrated at 45° C. under reduced pressure distilling about 600 mL of solvent.

Oxalic acid dihydrate (190.06 g) is added to the remaining organic solution and it is stirred for 1 hour.

The resulting solid is filtered, washed with 300 mL CH₂Cl₂ and dried at 45° C. and under reduced pressure for 16 hours.

The solid is re-suspended in 1.35 L acetonitrile (CH₃CN), it is brought to reflux for 15 minutes, then cooled to 25° C.

The mixture is filtered, washed with 450 mL CH₃CN, the solid is dried at 45° C. and under reduced pressure, obtaining 358.9 g of crystalline powder (intermediate 6-OX) which the elemental analysis shows as consisting of 63.18% carbon, 6.44% hydrogen, 5.43% nitrogen, 24.73% oxygen.

332.0 g bioxalate intermediate (6-OX) are suspended in 2324 mL CH₂Cl₂; a saturated aqueous solution of NaHCO₃ is added dropwise to the suspension, obtaining the complete solubilization of the solid (pH of the aqueous phase equal to 4.7).

The biphasic solution is filtered, the phases are separated and the organic phase is washed with saturated aqueous solution of NaCl (300 mL).

The organic phase is concentrated by distilling to ⅔ of the volume, 700 mL t-butyl alcohol (tBuOH) are loaded; it is distilled up to complete elimination of CH₂Cl₂ and of 120 mL tBuOH. Product precipitation is observed.

581 mL water are loaded and the mixture is brought to reflux. It is cooled to 20<T<25° C., the solid is filtered and washed with 230 mL of tBuOH/water 1/1 mixture, obtaining 293.2 g of wet product.

A sample dried for analytical purposes and analyzed by HPLC shows a chromatographic purity of 99.55%; the HPLC graph is shown in FIG. 1.

290 g of wet product are admixed with 506.5 mL tBuOH and 506.5 mL water, the mixture is brought to reflux for a few minutes, it is cooled to 20<T<25° C., the solid is filtered and washed with 200 mL of tBuOH/water 1/1 mixture.

It is dried in an oven at 50° C. under reduced pressure up to constant weight (192.1 g)

Figure 2:
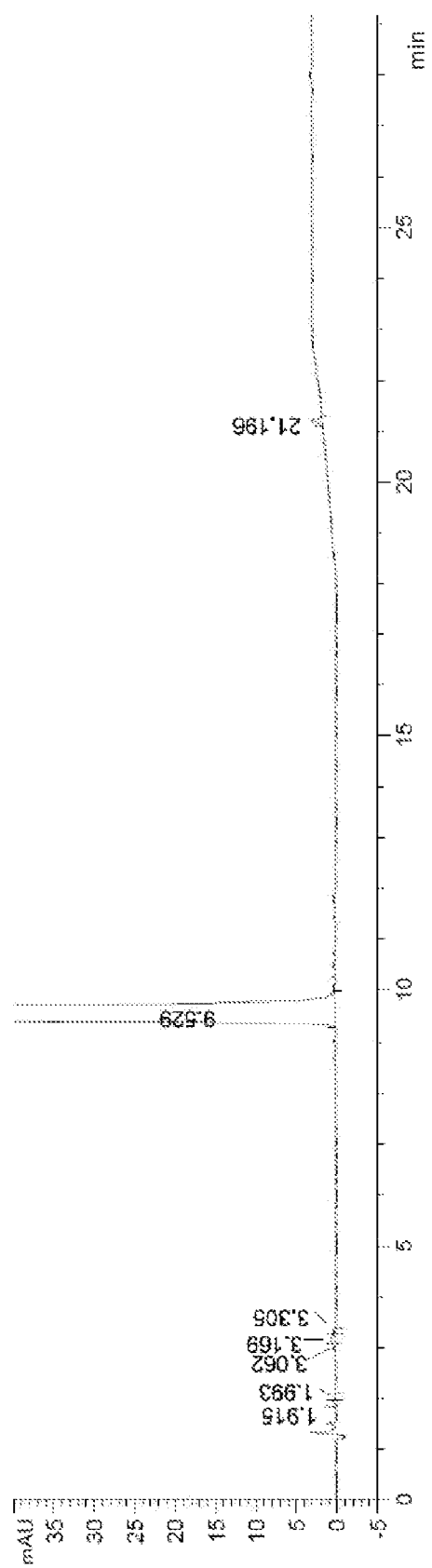

The product analyzed by HPLC shows a chromatographic purity of 99.73%; the HPLC graph is shown in FIG. 2. 190 g of product are solubilized under reflux with 1235 mL (6.5 volumes) of methyl alcohol, MeOH.

95 mL solvent are distilled, then it is cooled to 0° C. for 1 hour. It is filtered and washed with 100 mL cold MeOH. It is dried at 50° C. under reduced pressure for 16 hours.

Figure 3:
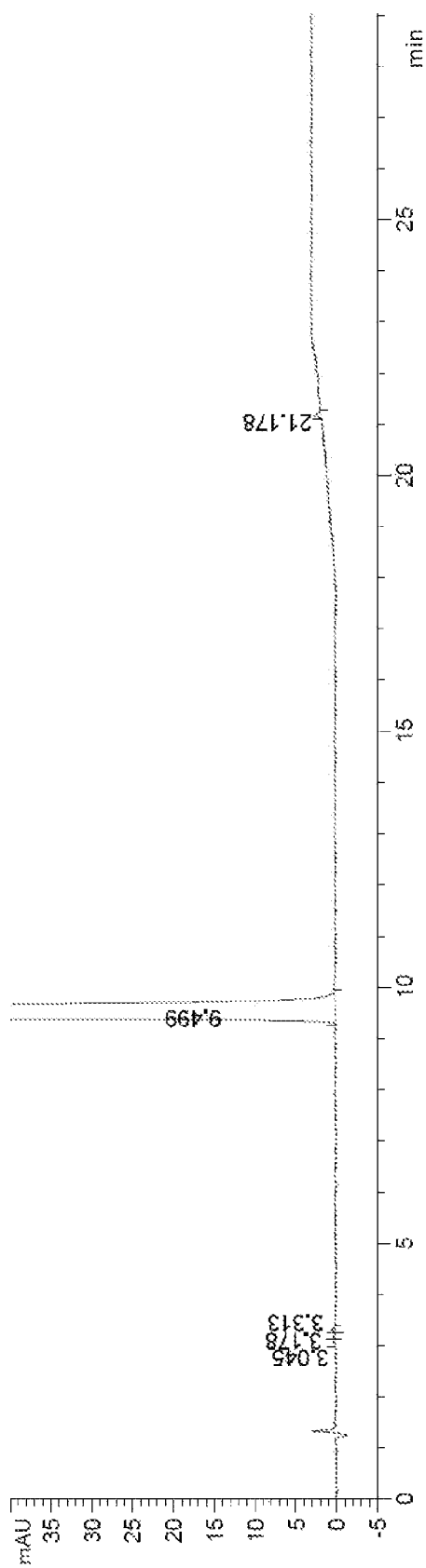

163.4 g Galeterone with an HPLC purity of 99.83% are obtained; the HPLC graph is shown in FIG. 3.

Example 2

Under nitrogen, 500 mg 17-iodoandrosta-5,16-dien-3β-ol (I), 12 mg CuI, 430 mg K₂CO₃, 180 mg benzimidazole, 5 mL DMF and 18 mg 8-hydroxyquinoline are loaded to a glass reactor of the Easy max system by Mettler Toledo and it is brought to reflux for 16 hours.

At a TLC check carried out at the end of this period, the reaction is complete.

The crude sample is chromatographed on silica gel eluting with a mixture of methylene chloride/methanol 9/1. The fractions containing product are concentrated to dryness and refluxed in pure methanol up to dissolution. After cooling, a crystalline solid is filtered which, dried to constant weight, turns out to be pure Galeterone (227 mg).

Example 3

The procedure of Example 2 is repeated with the only difference that DMSO (5 mL) is used as solvent instead of DMF.

At a TLC check carried out at the end of the reaction, this latter is complete.

Example 4

The procedure of Example 2 is repeated with the only difference that DMPU (5 mL) is used as solvent instead of DMF.

At a TLC check carried out at the end of the reaction, this latter is complete.

Example 5

The procedure of Example 2 is repeated with the only difference that 344 mg K$_2$CO$_3$ (68.8% by weight with respect to compound (I)) is used.

At a TLC check carried out at the end of the reaction, this latter is complete.

Example 6

The procedure of Example 2 is repeated with the only difference that 258 mg K$_2$CO$_3$ (51.6% by weight with respect to compound (I)) is used.

At a TLC check carried out at the end of the reaction, this latter is complete.

Example 7

The procedure of Example 2 is repeated with the only difference that DMA (5 mL) is used as solvent instead of DMF.

At a TLC check carried out at the end of the reaction, this latter is nearly complete, with about 15% of non-reacted compound (I).

Example 8

The procedure of Example 2 is repeated but using 2.5 mL DMF solvent.

At a TLC check carried out at the end of the reaction, this latter is complete.

Example 9

The procedure of Example 2 is repeated but using 6 mg CuI

At a TLC check carried out at the end of the reaction, this latter is partially complete.

Example 10

The procedure of Example 2 is repeated but using 9 mg of 8-hydroxyquinoline.

At a TLC check carried out at the end of the reaction, this latter is partially complete.

The invention claimed is:

1. A process for the preparation of 3β-hidroxy-17-(1H-benzimidazol-1-yl)androsta-5,16-diene (6) (Galeterone) comprising the reaction between 17-iodoandrosta-5,16-dien-3β-ol (I) and benzimidazole in the presence of an organic solvent, a base, cuprous iodide and 8-hydroxyquinoline:

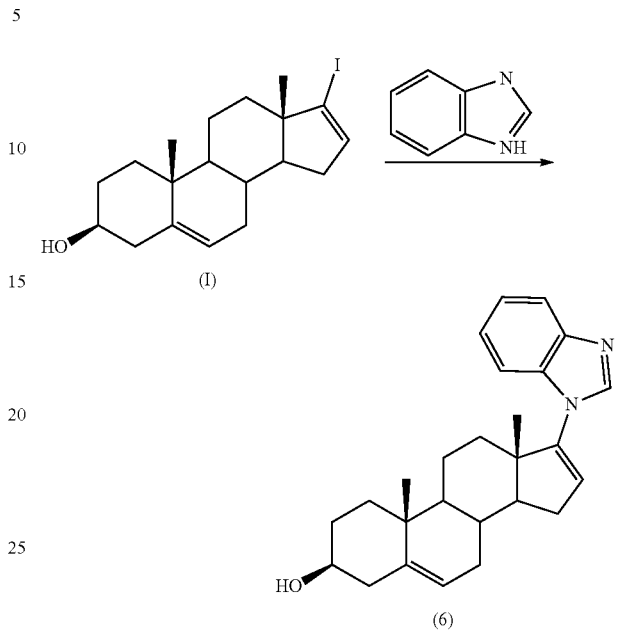

wherein 8-hydroxyquinoline is employed in an amount of at least 1.8% by weight with respect to compound (I) and cuprous iodide (CuI) is used in an amount between 1.2% and 5% by weight with respect to compound (I) employed in the reaction.

2. The process according to claim 1, wherein benzimidazole is used in an amount of at least 30% by weight with respect to compound (I).

3. The process according to claim 2, wherein benzimidazole is used in an amount of at least 36% by weight with respect to compound (I).

4. The process according to claim 1, wherein 8-hydroxyquinoline is used in an amount of 3.6% by weight with respect to compound (I).

5. The process according to claim 1 wherein the amount of cuprous iodide is equal to 2.4% by weight with respect to compound (I).

6. The process according to claim 1, wherein said base is selected among sodium carbonate, potassium carbonate, cesium carbonate, potassium tert-butoxide, sodium tert-butoxide, sodium hydroxide and potassium hydroxide, and is employed in an amount of at least 40% by weight with respect to compound (I).

7. The process according to claim 6, wherein the base is employed in an amount of at least 80% by weight with respect to compound (I).

8. The process according to claim 1, wherein said base is potassium carbonate (K$_2$CO$_3$).

9. The process according to claim 1, wherein the organic solvent is selected among dimethylformamide (DMF), dimethylacetamide (DMA), dimethylsulfoxide (DMSO) and 1,3-dimethyl-3,4,5,6-tetrahydro-2(1H)-pirimidinone (DMPU).

10. The process according to claim 9, wherein the solvent is dimethylformamide, employed in an amount between 5 and 20 times by volume, measured in milliliters, with respect to the weight in grams of compound (I).

11. The process according to claim 1, wherein the reaction temperature is between 130° C. and 200° C.

12. The process according to claim 11, wherein the reaction temperature is between 140° C. and the boiling temperature of the reaction mixture inclusive of all its components, wherein the reaction temperature does exceed 200° C.

13. The process according to claim 1, comprising the reaction between 17-iodoandrosta-5,16-dien-3β-ol (I) and benzimidazole in dimethylformamide (DMF) in the presence of potassium carbonate, cuprous iodide and 8-hydroxyquinoline, wherein the reaction is conducted under reflux for 16 hours.

14. A process for the preparation of a physiologically acceptable salt of 3β-hidroxy-17-(1H-benzimidazol-1-yl) androsta-5,16-diene (6) (galeterone) comprising:

the reaction between 17-iodoandrosta-5,16-dien-3β-ol (I) and benzimidazole in the presence of an organic solvent, a base, cuprous iodide and 8-hydroxyquinoline:

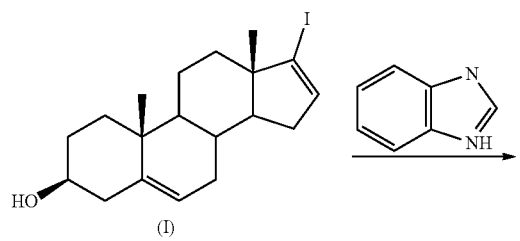

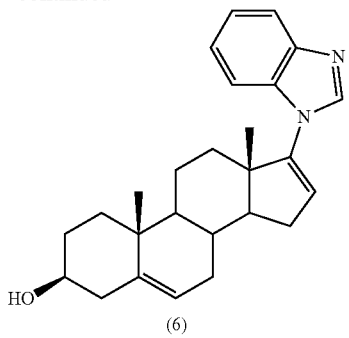

wherein 8-hydroxyquinoline is employed in an amount of at least 1.8% by weight with respect to compound (I) and cuprous iodide (CuI) is used in an amount between 1.2% and 5% by weight with respect to compound (I) employed in the reaction; and a step of precipitation of the compound obtained by reaction between galeterone and a physiologically acceptable acid, and separation of this compound from the reaction mixture by filtration to obtain said physiologically acceptable salt of galeterone.

15. The process according to claim 14, wherein the acid used is oxalic acid dihydrate.

\* \* \* \* \*